United States Patent [19]

Adams et al.

[11] Patent Number: 5,039,790

[45] Date of Patent: Aug. 13, 1991

[54] BIOACTIVE FRAGMENT OF INTERLEUKIN-1-B THAT HAS ANTAGONISTIC ACTIVITY

[75] Inventors: Steven P. Adams, St. Charles; Joseph W. Bulock, St. Peters; Kam F. Fok, St. Louis, all of Mo.

[73] Assignee: Monsanto Company, St. Louis, Mo.

[21] Appl. No.: 295,879

[22] Filed: Jan. 11, 1989

[51] Int. Cl.$^5$ .................. C07K 7/00; A61K 37/02
[52] U.S. Cl. ...................... 530/324; 530/345; 530/351; 530/405; 530/409; 514/2; 514/12; 424/85.1; 424/85.2
[58] Field of Search ............. 530/324, 345, 351, 405, 530/409, 806; 514/2, 12; 424/85.1, 85.2

[56] References Cited

U.S. PATENT DOCUMENTS

| | | | |
|---|---|---|---|
| 4,762,914 | 8/1988 | Auron et al. | 530/351 |
| 4,766,069 | 8/1988 | Auron et al. | 435/69.52 |
| 4,772,685 | 9/1988 | Schmidt | 530/351 |
| 4,774,320 | 9/1988 | Tagliabue et al. | 530/351 |
| 4,935,343 | 6/1990 | Allison et al. | 435/7 |
| 4,994,553 | 2/1991 | Schmidt | 530/351 |

FOREIGN PATENT DOCUMENTS 0237967  9/1987  European Pat. Off. .

OTHER PUBLICATIONS

Boraschi et al, *Biotherapy*, 1989, pp. 377–389.
Huang et al, *Mol. Biol. Med.* 4(3), 1987, pp. 169–181.
Kamagashira et al, *J. Biochem* 1988, 104(5) pp. 837–840.
March et al, *Nature* 315, 1985, pp. 641–647.
Mosley et al, *PNAS* 84, 1987, pp. 4572–4576.
Yem et al, *Lymphokine Res.* vol. 7(2) 1988, pp. 85–92.
Dinarello et al. *J. Immunol.* 133(3) 1984, p. 1332–1338.
Rimsky et al, *J. Immunol.* 136(9) 1986, pp. 3304–3310.
Lillquist et al, *J. Immunol.* 141(6) 1988, pp. 1975–1981.
Antoni, G. et al. *J. of Immunol.* 137:3201(1986).
Ferreira, S. H. et al. *Nature* 334:698 (1988).
Rosenwasser L. J. et al, *Proc. Natl. Acad. Sci. USA* 83:5243 (1986).
Boraschi, D. et al. *J. Exp. Med.* 168:675 (1988).
Palaszynski, E. W., *Biochem. and Biophys. Res. Comm.* 147:204 (1987).
Auron, P. E., et al, *J. Mol. Cell. Immunol.* 2:169 (1985).

*Primary Examiner*—Garnette D. Draper

[57] ABSTRACT

The present invention discloses a peptide capable of blocking activity of Interleukin-1. The peptide corresponds to the 157–186 amino acid residue of the IL-1β molecules.

14 Claims, No Drawings

BIOACTIVE FRAGMENT OF INTERLEUKIN-1-B THAT HAS ANTAGONISTIC ACTIVITY

BACKGROUND OF THE INVENTION

The lymphokine Interleukin-1 (IL-1) is produced naturally by activated mononuclear phagocytes and is involved in the development and maintenance of the inflammatory response. IL-1 includes both IL-1alpha (IL-1α) and IL-1beta (IL-1β). IL-1 plays an active role as mediator of host immunological and defense functions. IL-1 has the ability to stimulate T cells and B cells (Lymphocytes responsible for cellular immunity processes). IL-1 has been implicated as playing a role in many physiological responses including rheumatoid arthritis, fever induction, bone resorption, modulation of the central nervous system, alteration of corticosterone levels and glucose homeostasis. These attributes of IL-1 make it a candidate for pharmaceutical applications and the like. Nevertheless, the variety of biological effects of IL-1 makes the clinical exploitation of these factors difficult.

It is generally accepted that for many polypeptides, like IL-1, distinct domains exist which are responsible for binding activity with specific cellular receptors that mediate biological activity. The ability to locate active sites responsible for particular biological functions will enable the use of such active sites in pharmaceutical and therapeutic applications.

The nucleic acid sequence encoding human Interleukin-1 is known and has been cloned, Auron et al., U.S. Pat. No. 4,766,069. Auron et al., U.S. Pat. No. 4,762,914, describe vector sequences encoding the 1–197 and 136–197 amino acid residues of IL-1β. These biologically active human IL-1 proteins obtained via the cloned truncated IL-1 cDNA sequences can be used in the same manner as native human IL-1. Tagliabue et al, U.S. Pat. No. 4,774,320, disclose a synthetic peptide corresponding to the 163–171 amino acid residue of the IL-1 protein that has human Interleukin-1 activity which can be used as a stimulant of the immune functions.

SUMMARY OF THE INVENTION

It has now been discovered that a biologically active thirty (30) amino acid peptide of IL-1β blocks the action of IL-1. The peptides of this invention have the following amino acid sequence:

Val—Phe—Ser—Met—Ser—Phe—Val—Gln—Gly—Glu—Glu—Ser—Asn—Asp—Lys—Ile—Pro—Val—Ala—Leu—Gly—Leu—Lys—Glu—Lys—Asn—Leu—Tyr—Leu—Ser, the C-terminal amide thereof, and pharmaceutically acceptable salts thereof. The sequence is such that the left end is the amino terminal end and the right end is the carboxy-terminal end.

The peptides of this invention correspond to the 157–186 amino acid region of the IL-1β molecule and block IL-1 activity at nanomolar concentrations. The blocking activity includes the blocking of the upregulation of complement factor B gene expression and down regulation of albumin gene expression. The blocking activity also includes the blocking of the action of IL-1α and IL-1β.

The following chart describes the abbreviation for amino acids as used herein:

| AMINO ACID | One Letter Abbreviation | Three Letter Abbreviation |
|---|---|---|
| Alanine | A | Ala |
| Asparagine | N | Asn |
| Aspartic Acid | D | Asp |
| Glutamine | Q | Gln |
| Glutamic Acid | E | Glu |
| Glycine | G | Gly |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Tyrosine | Y | Tyr |
| Valine | V | Val |

The peptides of the invention may be obtained by genetic engineering techniques well known in the art. In addition, the peptide may be synthesized using known classical procedures and automated instrumentation. The method of obtaining the peptide is not critical to the invention. The peptide of the invention was synthesized by the solid phase method of Merrifield (*J. Amer. Chem. Soc.*, 1963, 85:2149).

A preferred peptide of the invention is the carboxy-terminal carboxyamide form of the peptide. Other groups may be added to the carboxy-terminus end. Such groups that are well known to those in the art include alcohols, amides, esters, aldehydes, anilides and various derivatives thereof. Therefore, the carboxy-terminal serine can be serine amide, serine anilide, serine methyl ester, serinal, serinol and the like. Likewise, the peptide may be used in its carboxylate form. A peptide with blocking activity of IL-1 yields the potential for treating the various physiological responses that flow from IL-1 activity, like rheumatoid arthritis and various other autoimmune diseases.

The peptides of the invention could be used in a variety of therapeutic and pharmaceutical applications. The peptide may be used for the preparation of pharmaceutical compositions in a pharmaceutically acceptable salt thereof, or an excipient therefor which can be used for therapeutic treatment. The pharmaceutical compositions may be prepared by any of the known procedures as described in Remington's Pharmaceutical Sciences, Mack Publishing Company, Eaton, Pa. 16th Ed., 1980. Non-toxic pharmaceutically acceptable salts that may be used and still maintain the biological activity of the parent compound include those formed with hydrochloric acid, nitric acid, cobalt, nickel, phosphoric acid, tartaric acid, zinc and zinc tannate. Excipients may include sterile water, saline, and buffered saline including buffers like phosphate or acetate, sodium chloride or sucrose as pressure adjusting agents, and antioxidants such as ascorbic acid, or any acceptable combinations thereof. The pharmaceutical composition may be in various forms like tablets and solutions and be administered by various routes including orally, nasally, and parenterally (including intravenously, intramuscularly, subcutaneously and intraperitoneally). The dose range will vary depending on variables like the patient's age, weight, condition, and route of administration. Typically, dose range is from 0.001 to 100 mg of active substance per kilogram body weight. Preferably the range is from 0.01 to 50 mg of active substance per kilogram body weight.

DESCRIPTION OF THE PREFERRED EMBODIMENTS

The following examples illustrate specific embodiments of the invention described herein. As would be apparent to skilled artisans, various changes and modifications are possible and are contemplated within the scope of the invention described.

EXAMPLE 1

PEPTIDE SYNTHESIS

A. Synthesis of the 157–186 IL-1β Fragment
The amide peptide of the following formula:

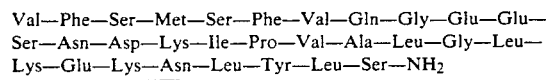

Val—Phe—Ser—Met—Ser—Phe—Val—Gln—Gly—Glu—Glu—
Ser—Asn—Asp—Lys—Ile—Pro—Val—Ala—Leu—Gly—Leu—
Lys—Glu—Lys—Asn—Leu—Tyr—Leu—Ser—NH$_2$ is synthesized by the solid phase method of Merrifield (*J. Amer. Chem. Soc.* 85, pp. 2149–2154, 1963) using methylbenzhydrylamine (MBHA) resin, and a 430A automated peptide synthesizer (Applied Biosystems, Inc., Foster City, Calif.). The solid phase method provides a solid support (usually a styrene/vinylbenzene copolymer) on which one stepwise builds the peptide chain while still using many of the classical peptide synthesis reagents and protecting groups.

The amino acids, N-protected amino acids, (Applied Biosystems, Inc., Foster City, Calif.) are first coupled to the resin and then to the growing peptide chain with symmetrical anhydrides formed with dicyclohexylcarbodiimide, except for amino acids asparagine and glutamine. For asparagine and glutamine, the 1-hydroxybenzotriazole active esters are utilized. A total of 0.5 mmole of MBHA resin (substitution 0.45 mmole/gram) is used. The activated amino acid used is in 2-fold excess. The tert-butyloxycarbonyl groups are removed by trifluoroacetic acid, followed by neutralization with diisopropylethylamine to form the free amine. This amine can then react with the activated carboxyl group of the next amino acid. In this particular case double coupling of amino acids is used. After a brief wash of the resin-peptide, a new charge of activated amino acid is introduced to increase the coupling efficiency.

B. Removal and Purification

At completion of the synthesis, the peptide is deprotected and removed from the resin with anhydrous HF in the presence of anisole and dimethyl sulfide (both 10% v/v) at about 0° C. for 1 hour. The crude peptide was extracted from the resin with 33% acetic acid/water and lyophilized. The crude peptide is purified on a C$_{18}$ reverse phase low pressure column (Vydac 15–20 micron [The Separations Group, Hesperia, Calif.]) with a 5–40% acetonitrile/water gradient (with 0.05% trifluoroacetic acid in both solvents). The desired fractions are collected, combined and lyophilized. The purity of the peptide is verified with analytical reverse phase HPLC on a C$_{18}$ Vydac column (4.6 mm×250 mm) using a linear gradient of 20–50% acetonitrile (0.05% TFA) in water (0.05% TFA) over 30 minutes. The flow rate is 1.5 ml/min. The structure of the peptide is verified by amino acid composition, peptide sequencing and mass spectrometry. The 163–171 amino acid fragment of IL-1β is synthesized in the same manner as the 157–186 fragment.

EXAMPLE 2

Biological Assay

A. Agonistic Effect

Human HepG2 cells are incubated at 37° C. for 18–24 hours in serum-free Dulbecco's modified Eagle medium. Separate monolayers of cells are incubated in the same medium supplemented with the IL-1β fragment at various concentrations and in the same medium supplemented with intact recombinant human IL-1β at various concentrations.

Monolayers are rinsed vigorously with isotonic buffer and incubated in (35-S) methionine, 250 μci/ml methionine-free medium and pulsed for a period of 15–30 minutes to assess net synthesis. Cell culture fluid is discarded and monolayers are again rinsed and resuspended in cell lysis buffer. The newly synthesized radiolabelled hepatic proteins in these cell lysates are detected by immunoprecipitation, SDS-PAGE and fluorography. The 163–171 fragment is tested in a similar manner. In some experiments a 15-amino acid peptide corresponding to residues 172–186 has partial agonistic activity at micromolar concentrations. There is a suboptimal (2- to 3-fold) increase in factor B gene expression at 250 ug/ml peptide as contrasted to the 9- to 10-fold increase in factor B gene expression elicited by 500 pg/ml intact IL-1. The 157–186 fragment peptide has no agonistic activity. Finally, a 9-amino acid peptide corresponding to residues 163–171 has no agonistic activity. See Table 1.

B. Antagonistic Effect

Human HepG2 cells are incubated at 37° C. for 18–24 hours in serum-free Dulbecco's modified Eagle medium, or medium supplemented with intact Separate monolayers of cells are incubated in medium supplemented with intact IL-1 and various concentrations of the IL-1β 157–186 fragments. Net synthesis of hepatic plasma proteins is determined as described in Section A. The 163–171 fragment is tested in a similar manner. The 157–186 peptide blocks the action of human recombinant IL-1β at nanomolar concentrations (lowest concentration tested 5 ng/ml peptide vs. 500 pg/ml intact IL-1; 3 nM peptide vs. 30 pM intact IL-1). The antagonistic effect is highly specific in that there is blocking of the up-regulation of complement factor B gene expression and down-regulation of albumin gene expression in the same experiment. There is blocking of the action of IL-1α and IL-β but not that of TNF-alpha. The antagonistic effect is apparent if the peptide is added 6 hours prior to or simultaneously with the addition of intact IL-1. Its effect is still evident, although reduced, if it is added 3 hours after intact IL-1. The 9-amino acid peptide corresponding to residues 163–171 has no antagonistic activity. Taken together, the results suggest that a region of 30-amino-acids (157–186) within the IL-1 molecule can be used to provide synthetic antagonistic activity at low (nanomolar) concentrations. Much higher concentrations are necessary to demonstrate antagonistic activity of a shorter peptide based on the sequence in the same region. See Table 1.

TABLE 1

| IL-1 Fragment | Agonist | Antagonist | Concentration microgram/ml |
|---|---|---|---|
| 163–171 .VQGEESNDK-NH$_2$ | No | No | — |

TABLE 1-continued

| IL-1 Fragment | Agonist | Antagonist | Concentration microgram/ml |
|---|---|---|---|
| 157–171<br>VFSMSFVQ<br>GEESNDK-NH₂ | No | Yes | 50 |
| 157–186<br>VFSMSFVQGEES<br>NDKIPVALGLKE<br>KNLYLS-NH₂ | No | Yes | .005 |
| 172–186<br>IPVALGLKEKNLYLS-NH₂ | Yes | No | 250 |

What is claimed is:

1. A peptide selected from the group consisting of:

Val—Phe—Ser—Met—Ser—Phe—Val—Gln—Gly—Glu—
Glu—Ser—Asn—Asp—Lys—Ile—Pro—Val—Ala—Leu—
Gly—Leu—Lys—Glu—Lys—Asn—Leu—Tyr—Leu—Ser, the C-terminal amide thereof, and pharmaceutically acceptable salts thereof.

2. The peptide of claim 1 of the formula:

Val—Phe—Ser—Met—Ser—Phe—Val—Gln—Gly—Glu—
Glu—Ser—Asn—Asp—Lys—Ile—Pro—Val—Ala—Leu—
Gly—Leu—Lys—Glu—Lys—Asn—Leu—Tyr—Leu—Ser.

3. The peptide of claim 1 in which the peptide is the C-terminal amide.

4. The peptide of claim 2 comprising the pharmaceutically acceptable salts thereof.

5. The peptide of claim 3 comprising the pharmaceutically acceptable salts thereof.

6. A pharmaceutical composition comprising a pharmaceutically acceptable excipient and a therapeutically effective amount of a peptide selected from the group consisting of:

Val—Phe—Ser—Met—Ser—Phe—Val—Gln—Gly—Glu—
Glu—Ser—Asn—Asp—Lys—Ile—Pro—Val—Ala—Leu—
Gly—Leu—Lys—Glu—Lys—Asn—Leu—Tyr—Leu—Ser, the C-terminal amide thereof, and pharmaceutically acceptable salts thereof.

7. The pharmaceutical composition of claim 6 in which the peptide is selected from the group consisting of:

Val—Phe—Ser—Met—Ser—Phe—Val—Gln—Gly—Glu—
Glu—Ser—Asn—Asp—Lys—Ile—Pro—Val—Ala—Leu—
Gly—Leu—Lys—Glu—Lys—Asn—Leu—Tyr—Leu—Ser, and pharmaceutically acceptable salts thereof.

8. The pharmaceutical composition of claim 6 in which the peptide is selected from the group consisting of the C-terminal amide and pharmaceutically acceptable salts thereof.

9. A method for blocking IL-1 related physiological responses which comprises administering an IL-1 effective amount of a peptide selected from the group consisting of:

Val—Phe—Ser—Met—Ser—Phe—Val—Gln—Gly—Glu—
Glu—Ser—Asn—Asp—Lys—Ile—Pro—Val—Ala—Leu—
Gly—Leu—Lys—Glu—Lys—Asn—Leu—Tyr—Leu—Ser, the C-terminal amide thereof, and pharmaceutically acceptable salts thereof.

10. The method of claim 9 in which the peptide is of the formula:

Val—Phe—Ser—Met—Ser—Phe—Val—Gln—Gly—Glu—
Glu—Ser—Asn—Asp—Lys—Ile—Pro—Val—Ala—Leu—
Gly—Leu—Lys—Glu—Lys—Asn—Leu—Tyr—Leu—Ser.

11. The method of claim 9 in which the peptide is the C-terminal amide.

12. The method of claim 10 in which the peptide is administered as a pharmaceutically acceptable salt.

13. The method of claim 11 in which the peptide is administered as a pharmaceutically acceptable salt.

14. The method of claim 9 in which the peptide is administered as a pharmaceutical composition comprising a pharmaceutically acceptable excipient.

* * * * *